United States Patent [19]

Johnson

[11] Patent Number: 4,609,373
[45] Date of Patent: Sep. 2, 1986

[54] SANITARY NAPKIN WITH ATTACHMENT MEANS

[75] Inventor: Russell L. Johnson, Waupaca County, Wis.

[73] Assignee: Kimberly-Clark Corporation, Neenah, Wis.

[21] Appl. No.: 538,611

[22] Filed: Oct. 3, 1983

[51] Int. Cl.[4] .............................................. A61F 13/16
[52] U.S. Cl. ................................ 604/389; 604/385 R; 604/390; 604/387
[58] Field of Search ................................ 604/389–399

[56] References Cited

U.S. PATENT DOCUMENTS

| | | | |
|---|---|---|---|
| 1,168,679 | 1/1916 | Rutherford | 604/398 |
| 2,032,131 | 2/1936 | Kennard | 604/397 |
| 2,516,331 | 7/1950 | Miles | 604/398 |
| 3,704,710 | 12/1972 | Fifer | 604/398 |

Primary Examiner—John D. Yasko
Assistant Examiner—Sherri E. Vinyard
Attorney, Agent, or Firm—Paul A. Leipold; Donald L. Traut; J. J. Duggan

[57] ABSTRACT

A means for attaching a perineal pad to a support garment so as to restrict the range of possible displacement of the pad while not transferring dynamic loads from the garment to the pad and being characterized by a tab secured to the garment side of the pad near one end of the longitudinal midline of the pad. The tab has adhesive on the pad side of its free end so that, in use, after the tab has been passed through a loop provided on the support garment the free end of the tab may be adhered to the garment side of the pad and thereby create a loop coupling between the pad and the garment.

4 Claims, 2 Drawing Figures

SANITARY NAPKIN WITH ATTACHMENT MEANS

FIELD OF THE INVENTION

This invention relates to a sanitary napkin and particularly one with unique means for attaching a sanitary napkin to an undergarment.

BACKGROUND OF THE INVENTION

Generally sanitary napkins have been attached by two general methods, first, sanitary napkins have been provided with end extensions or tabs which are engaged by a supporting belt. The other major method for attachment for the so-called tabless sanitary napkins employs pressure sensitive adhesives positioned on the garment facing side of the napkin which, depending upon the particular napkin chosen would be either a fluid impervious baffle or a fluid permeable wrap which overlies the baffle. This adhesive is designed to directly engage the undergarment of the wearer.

Another approach has been to utilize a sanitary napkin with attachment means functioning in combination with an undergarment having some sort of reciprocal means for maintaining this attachment. Representative samples of these combinations can be found in U.S. Pat. Nos. 3,749,095; 3,704,710; 3,460,535; 2,949,114; 3,420,236; and 2,890,701 as well as British Pat. No. 862,763.

U.S. Pat. Nos. 3,420,236 and 2,890,701 disclose undergarments with loops which provide for fixed attachment of sanitary napkins.

One of the problems with the tabless napkins and the sanitary napkins utilizing attachment means provided in the napkin themselves is that movement by the wearer tends to provide forces such as shear which tend to dislodge the napkin from its proper position. These forces are exerted because of the essentially static permanent position of the napkin with respect to bodily movement of the wearer.

SUMMARY OF THE INVENTION

According to this invention a sanitary napkin is provided with a coupling attachment means which when engaging a suitably constructed undergarment provides for the relative cooperative movement of the sanitary napkin with regard to both the support garment and the wearer's body.

The invention, in its simplest form, may be described as a loop coupling means for a sanitary napkin which cooperates with a closed loop provided on the support garment. By the selective positioning and attachment of the open loop provided on the sanitary napkin, the desired relative movement is accomplished.

DETAILED DESCRIPTION OF THE INVENTION AND DRAWINGS

Figure 1:
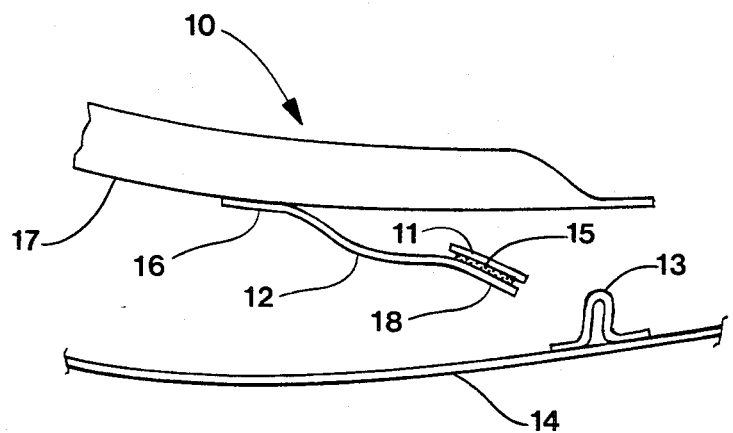
Figure 2:
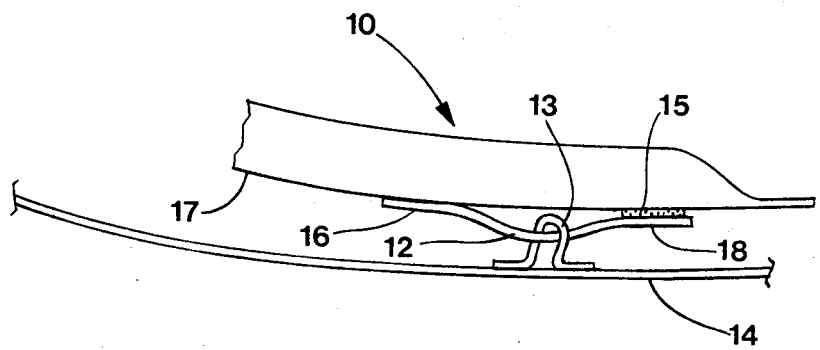

The invention may more readily be understood by reference to the drawings in which FIG. 1 is a diagrammatic elevational view showing the closeable loop of the invention; and FIG. 2 is a sectional elevation view of the coupling of FIG. 1 after the closed loop of the sanitary napkin has been positioned through the adapted undergarment.

As can be seen by reference to the drawings sanitary napkin 10 has a strip 12 which is of a strong yet flexible material permanently attached at one end 16 to the garment side 17 along the central longitudinal axis of the napkin and at a suitable distance from the end of napkin 10. Strip 12 has a free end 18 with closure 15 which may be any refastenable means such as snaps, hooks, or as shown, adhesive with release paper 11 or the like.

In use, as can be seen in FIG. 2, the free end 18 of the strip 12 is passed through the closed loop 13 of the matched garment 14 and then secured by means of attachment 15 to the garment facing side of pad 10 thereby coupling pad 10 to garment 14 but allowing the pad 10 to slide along the unattached length of strip 12.

It may be desirable depending upon the size of the napkin, to utilize a plurality of strip 12 and loop 13 combinations. Generally, however, two combinations are sufficient to provide for napkin movement without displacement of the napkin relative to the wearer.

What is claimed is:

1. A coupling for attaching a sanitary napkin to the crotch area of an undergarment, comprising:
   means for forming a loop on the undergarment in the crotch area, and
   means for forming a loop on the sanitary napkin, said sanitary napkin loop means engaging said undergarment loop means to attach said sanitary napkin to said undergarment wherein said means for forming a loop on the sanitary napkin comprises an elongated member having a first end attached to said sanitary napkin, a second end that is initially free to pass through said undergarment loop means, and means for attaching said second end to the sanitary napkin after passing through said undergarment loop means to engage said undergarment loop means with said sanitary napkin loop means.

2. The coupling of claim 1 wherein the crotch area of the undergarment has a center-line extending between a front and a back respectively corresponding to a frontside and a backside of a wearer, said undergarment loop means being located on said center-line, the sanitary napkin having a longitudinal axis which generally extends along said center-line when said napkin is in use, said elongated member extending along said longitudinal axis with said first and second ends spaced apart when attached to the sanitary napkin allowing the sanitary napkin to slide along said center-line relative to said undergarment loop means.

3. A coupling for attaching a sanitary napkin to the crotch area of an undergarment comprising:
   a first closed loop fastened to the crotch area of the undergarment; and
   a loop coupling means for attaching the sanitary napkin to said closed loop, said loop coupling means comprising a strip defining first and second ends, wherein said first end is fastened to the sanitary napkin and said second end is free to pass through said closed loop, and means for fastening said second end to the sanitary napkin to thereby form a second closed loop coupling the sanitary napkin to the undergarment.

4. A coupling for attaching a sanitary napkin to the crotch area of an undergarment which permits the sanitary napkin to move relative to the undergarment allowing freer movement of the sanitary napkin in association with body movement, comprising:
   a closed loop which is fastened to the crotch area of the undergarment at a point along a center-line extending between a front and a back of the crotch area respectively corresponding to a frontside and a backside of a wearer, and means for forming an extended loop on the sanitary napkin which is engageable with said undergarment loop, said sanitary napkin loop means comprising an elongated strip having a first end fixed to said sanitary napkin, a second end that is initially free to pass through said undergarment loop, and adhesive means to fix said second end to said sanitary napkin after passing through said undergarment loop, said sanitary napkin having a longitudinal axis which generally extends along said center-line when said napkin is in use, with said first and second ends of said elongated strip fixed to said sanitary napkin generally along said longitudinal axis at spaced apart points to form said extended sanitary napkin loop, the sanitary napkin thereby being able to slide along said center-line relative to said undergarment loop.

* * * * *